United States Patent [19]

Panneman

[11] 4,013,682
[45] Mar. 22, 1977

[54] N-HYDROXY-AMIDINE COMPOUNDS

[75] Inventor: Harm Jan Panneman, Oss, Netherlands

[73] Assignee: Akzona Incorporated, Asheville, N.C.

[22] Filed: May 24, 1976

[21] Appl. No.: 689,301

Related U.S. Application Data

[63] Continuation-in-part of Ser. No. 488,648, July 15, 1974, Pat. No. 3,978,126.

[30] Foreign Application Priority Data

Aug. 3, 1973 Netherlands .................. 7310741

[52] U.S. Cl. .......................... 260/340.5; 424/282
[51] Int. Cl.$^2$ ..................... C07D 317/44
[58] Field of Search ............. 260/340.5, 340.3

[56] References Cited

UNITED STATES PATENTS

| | | | |
|---|---|---|---|
| 3,405,138 | 10/1968 | Judd | 260/340.3 |
| 3,470,300 | 9/1969 | Skorcz | 424/282 X |
| 3,804,898 | 4/1974 | Panneman | 260/564 A |
| 3,867,447 | 2/1975 | Cherkofsky | 260/340.5 X |

Primary Examiner—Ethel G. Love
Attorney, Agent, or Firm—Francis W. Young; Philip M. Pippenger; Hugo E. Weisberger

[57] ABSTRACT

The invention relates to novel biologically active compounds of the formula I:

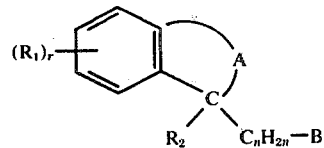

in which B is a N-hydroxy-amidino group of the general formula:

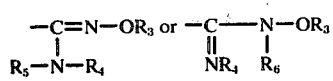

A represents a methylene-, ethylene- or propylene group, optionally substituted with lower alkyl groups
$r$ stands for the number: 0, 1, 2, 3 or 4
$R_1$ is hydroxy, alkyl, alkylthio or alkoxy, halogen (F, Cl, Br or I), trifluoromethyl, nitro, amino or alkylenedioxy (1-4 C),
$C_nH_{2n}$ is an alkylene group with 0–4 carbon atoms
$R_2$ stands for hydrogen, alkyl, aryl or aralkyl,
$R_3$, $R_4$, $R_5$ represent hydrogen, alkyl, aralkyl or acyl, and
$R_6$ stands for hydrogen, alkyl, or phenyl or benzyl optionally substituted with methyl groups and pharmaceutically acceptable acid addition salts thereof. The compounds possess anti-hypertensive and vasodilatory activities.

4 Claims, No Drawings

CROSS-REFERENCES TO RELATED APPLICATION

This application is a continuation-in-part of application Ser. No. 488,648, filed on July 15, 1974, now U.S. Pat. No. 3,978,126.

The invention relates to novel biologically active N-hydroxy-amidine compounds and to processes for the preparation thereof.

It was found that compounds of the general formula:

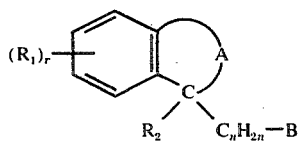

in which B is a N-hydroxy-amidino group of the general formula:

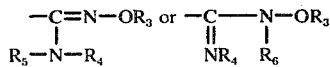

A. represents a methylene-, ethylene- or propylene-group, optionally substituted with lower alkyl groups r stands for the number 0, 1, 2, 3 or 4

$R_1$ is hydroxy, alkyl, alkylthio or alkoxy, halogen (F, Cl, Br or I), trifluoromethyl, nitro, amino or alkylenedioxy (1–4 C), $C_nH_{2n}$ is an alkylene group with 0–4 carbon atoms, $R_2$ stands for hydrogen, alkyl, aryl or aralkyl, $R_3$, $R_4$, $R_5$ represent hydrogen, alkyl, aralkyl or acyl, and $R_6$ stands for hydrogen, alkyl, or phenyl or benzyl optionally substituted with methyl groups as well as the acid addition salts thereof, are valuable biologically active compounds.

The compounds I possess antihypertensive and vasodilatory activities. In contrast to many other antihypertensive compounds they retain their activity in the case of oral administration. The compounds I possess further valuable anti-thrombosis activity, more particularly they inhibit the aggregation of blood-platelets, and induce an inhibition of the activity of the enzyme thrombine. Moreover the compounds I can be used for their biocidal activity.

It is to be understood that compounds of the general formula I, in which $r = 0$, are compounds without any substitution on the phenyl ring. Compounds I in which $r = 1$ are compounds bearing on the phenyl ring one of the substituents mentioned in the definition of $R_1$, whereas compounds I in which $r = 2$, 3 or 4 are compounds bearing on the phenyl ring two or more, identical or different substituents mentioned in the definition of $R_1$.

With an "alkyl group" or "lower alkyl group" is meant a branched or unbranched alkyl group of 1–6 carbon atoms, such as methyl, ethyl, propyl, isopropyl, butyl, isobutyl, tert. butyl, n.pentyl, isopentyl or hexyl.

The alkyl group in the alkoxy and alkylthio moieties has the same meaning.

An aralkyl group mentioned in the definition of $R_2$, $R_3$, $R_4$ and $R_5$ is preferably a phenylalkyl group in which the alkyl group contains 1–4 carbon atoms, such as benzyl, phenylethyl, phenylpropyl, phenylisopropyl, phenylbutyl and phenylisobutyl.

The aryl group mentioned in the definition of $R_2$ is preferably a phenyl group which may be substituted, such as phenyl, o-tolyl, p-tolyl, xylyl, etc.

An acyl group mentioned in the definition of $R_3$, $R_4$, $R_5$ is, in general, an acid-residue derived from an organic carboxylic acid with 1–18 carbon atoms, more particularly carbamic acids, lower aliphatic carboxylic acids of 1–6 carbon atoms and cyclo- or araliphatic carboxylic acids with 6–10 carbon atoms.

The compounds according to the general formula I can be prepared by any method commonly used for this type of compounds.

Most easily the compounds of the invention may be prepared by reacting the nitrile of formula II:

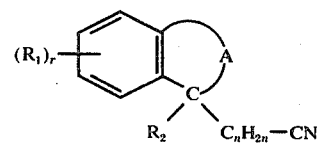

with hydroxylamine or a hydroxylamine derivative of the general formula III:

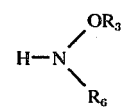

or an acid addition salt thereof, in which A, $R_1$, $r$, $R_2$, $C_nH_{2n}$, $R_3$ and $R_6$ have the meanings mentioned above.

Moreover the compounds I can be prepared by condensation of an O- or S-alkyliso(thio) amide of the general formula:

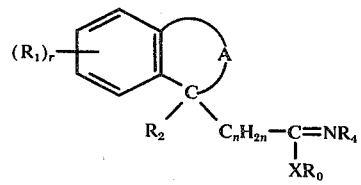

or an acid addition salt thereof, in which $R_1$, $r$, A, $R_2$, $C_nH_{2n}$ and $R_4$ have the meaning mentioned above, X is an oxygen- or sulphur atom and $R_o$ is a lower alkyl, preferably a methyl- or ethyl group, with hydroxylamine or a hydroxylamine derivative according to the general formula III or an acid addition salt thereof.

The starting material IV required in the last mentioned synthesis can be prepared, for example, from the corresponding acid chloride V:

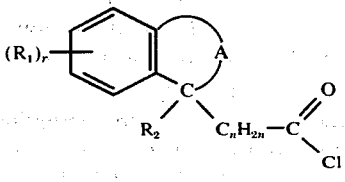

V

The acid chloride V is converted with ammonia or a primary amine into the corresponding primary or secondary amide, whereafter, if required, the oxygen atom of the carboxamide group is replaced by a sulphur atom by a method known per se, for example with $P_2S_5$ ($P_4S_{10}$). Both the carbothionamido-compound obtained in this way and the carboxamido-compound obtained earlier in the synthesis can be converted into the starting material IV by alkylation of the sulphur- or oxygen atom respectively, for example with an alkylhalide, preferably methyl-iodide or ethyliodide.

The starting material IV can further be prepared from the compound II in a very simple manner by reaction with methanol or ethanol, preferably under acidic conditions or in the presence of a catalyst.

Although the latter method (through compound IV) is to be preferred in view of higher yields and milder reaction conditions, the compounds according to the invention may also be prepared directly from the aforesaid carbothionamido compounds of the formula:

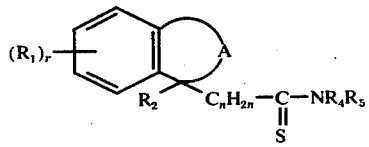

IV A by reacting (the thionamide) with hydroxylamine or a hydroxylamine derivative according to the general formula III or an acid addition salt thereof.

Finally the compounds I may be prepared starting from a compound of the general formula VI:

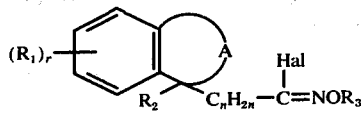

VI in which $R_1$, $r$, A, $R_2$, $R_3$ and $C_nH_{2n}$ have the meanings mentioned previously and Hal stands for halogen (F, Cl, Br, I), preferably a chloro or bromo group,
by reacting (VI) with ammonia or a primary or secondary amine of the general formula VII:

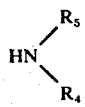

VII or an acid addition salt thereof, in which $R_4$ and $R_5$ have the aforesaid meanings.

The starting compound VI required for this reaction may be prepared in any conventional manner preferably by halogenating the corresponding aldoxime (obtained from the corresponding aldehyde).

Hydroxylamine or hydroxylamine derivatives according to formula III, required in the above mentioned condensation reactions, are for example hydroxylamine (free base), hydroxylaminemethylether, hydroxylamineethylether, hydroxylaminepropylether, hydroxylaminebenzylether, methylhydroxylamine, ethylhydroxylamine, isopropylhydroxylamine, benzylhydroxylamine, phenylhydroxylamine, o-tolyhydroxylamine, p-tolylhydroxylamine, methylhydroxylaminemethylether and the acid addition salts thereof.

Amines according to the general formula VII which can be used in the aforesaid condensation reaction with the compound VI are, for example, ammonia, methylamine, dimethylamine, ethylamine, isopropylamine, benzylamine, phenylethylamine, (N)benzyl(N)methylamine, phenylpropylamine, and the acid addition salts thereof.

Most optional substituents on the phenyl ring ($R_1$), on the nitrogen atoms ($R_4$, $R_5$, $R_6$) or on the oxygen atom ($R_3$), are preferably already present in one of the aforementioned starting compounds (II, IV or VI).

It is possible, however, to introduce or to modify these substituents in a subsequent reaction following the condensation reactions mentioned before. This holds especially for a possible acylation of the compounds of formula I.

For example the N-hydroxy group of a compound I (with $R_3 =$ H) may be (ar)alkylated in a conventional manner with, e.g., diazomethane, diazoethane, dimethylsulphate or by means of a Williamson synthesis. In a usual manner this N-hydroxy group may further be acylated with an organic carboxylic acid or preferably with a functional derivative thereof.

A nitrogen atom of the compounds I, in which at least one of the substituents $R_4$, $R_5$, $R_6$ is hydrogen, may be acylated in the usual way, for example with anhydrides, or (ar)alkylated, for example, with (ar)alkylhalides or by means of an Eschweiler-Clarke reaction.

It is further possible to modify certain substituents ($R_1$) on the phenyl ring of a compound I. A hydroxy group, for example, can be converted in a conventional manner into an alkoxy group, a nitro group into an amino group, an amino group into hydroxy or halogen, a methoxy group into a hydroxy group, etc.

The compounds of formula I have alkaline properties. Dependent on the reaction conditions in which they are prepared, they can be obtained as the free base or as an acid addition salt. However, if desired, the free base I can be prepared from the salt, for example, by reaction with an alkaline compound or by means of an ion-exchanger, while the free base can be converted into an acid addition salt in the usual manner.

Pharmaceutically acceptable acid addition salts are obtained by having the free base I reacted with acids, such as hydrochloric acid, sulphuric acid, phosphoric acid, acetic acid, propionic acid, glycollic acid, maleic acid, fumaric acid, malonic acid, succinic acid, tartaric acid, lactic acid, citric acid, ascorbic acid, salicylic acid, benzoic acid.

From the general formula I of the final products it appears that the compounds according to the invention contain an asymmetric carbon atom, which means that both racemic mixtures I as well as optically active compounds I are possible. These optically active compounds I also belong to the compounds according to the invention. They can be prepared either directly from an optically active starting product (II, IV, VI) or can be obtained by resolution of the racemic mixture I by a method commonly used for similar resolutions.

Compounds I, which are to be preferred in view of their antihypertensive and vasodilatory activities are characterized by the following definition (either alone or in combination):

A stands for an optionally substituted ethylene group and more particularly for an optionally substituted methylene group, r is the number 0, 1 or 2, preferably 0, $C_nH_{2n}$ stands for a methylene group and more preferably is completely absent ($n = 0$), $R_3$ represents hydrogen or a suitable acyl group, especially an acyl group derived from a carbamic acid or a lower aliphatic or araliphatic carboxylic acid, such as carbamoyl, N-methylcarbamoyl, N,N-dimethylcarbamoyl, N-ethylcarbamoyl, N-propylcarbamoyl, N-phenylcarbamoyl, N-benzylcarbamoyl, acetyl, propionyl, butyryl, pentanoyl, benzoyl, phenylacetyl or phenylpropionyl, $R_4$, $R_5$ and $R_6$ are hydrogen.

Compounds I which are to be preferred in view of their excellent antithrombosis activities are characterized by the following definitions either alone or in combination:

A stands for an optionally substituted methylene or ethylene group, r is the number 0, 1 or 2, preferably 1 or 2, $C_nH_{2n}$ stands for a methylene moiety or is absent ($n = 0$), $R_3$ represents hydrogen, $R_4$, $R_5$ and $R_6$ represent hydrogen or a lower alkyl group.

As already mentioned previously the acyl derivatives, in particular the O-acyl derivatives, of the general formula I, are preferably prepared by acylating a compound I (in which $R_3 = H$) in the usual manner, for example, with anhydrides such as acetic acid anhydride, propionic acid anhydride, butyric acid anhydride, phenyl acetic acid anhydride, etc. or with acid halides such as acetyl chloride, propionyl chloride, butyryl bromide, dimethylcarbamoyl chloride, phenylacetyl chloride, etc. The O-carbamoyl derivatives I, however, can also be prepared with cyanic acid or suitable salts, preferably alkali metal salts thereof, such as the sodium, potassium or lithium salt, or with isocyanates, particularly N-lower alkyl-isocyanates, N-phenylisocyanates and N-phenyl(lower)alkyl-isocyanates, such as N-methylisocyanate, N-ethylisocyanate, N-propylisocyanate, N-butylisocyanate, N-phenylisocyanate, N-p-tolylisocyanate, N-benzylisocyanate, N-phenylethylisocyanate, etc.

The preparation of the O-carbamoyl compounds according to the invention with the aid of an isocyanate takes place by converting the amidoxime I ($R_3 = H$) with an isocyanate at ambient temperature ($-20°$ C $- +50°$ C). Unsubstituted O-carbamoyl compounds I may be prepared by converting the amidoxime I with cyanic acid preferably in an aqueous solution or by converting an acid addition salt of the amidoxime I with an alkali-metal cyanate. In the latter conversion cyanic acid is formed in situ.

The compounds according to the invention can be administered orally, locally as well as parenterally, preferably in a daily dosage of from 0.001 to 50 mg per kg body weight. For this purpose the compounds are incorporated into a suitable dosage form for oral, local or parenteral administration, for example, a tablet, pill, capsule, solution, suspension, emulsion, paste or spray by a method commonly used for other, biologically active compounds.

A dosage form for oral administration is to be preferred.

The position of the double bond between the nitrogen and carbon atoms in group B of formula I cannot be unequivocally determined. Since tautomerism is posible (if $R_5$ and $R_6 = H$), an equilibrium occurs between the compounds:

As far as the nomenclature adopted in the examples is concerned and in so far as tautomerism can occur, it is taken for granted that principally the oxime will be obtained so that these compounds are indicated as carboxamidoxime derivatives. If tautomerism is not possible ($R_5$ or $R_6$ is other than hydrogen) the products are indicated as N-hydroxy-carboamidines.

EXAMPLE I a. Benzocyclobutene-1-carboxamidoxime and salts thereof 50 g of 1-cyano-benzocyclobutene (Org. Synth. 48, 92 (1968) are mixed with a solution obtained from 250 ml of methanol, 7 g of lithium and 70 g of hydroxylamine.hydrochloride. Stirring for 30 minutes raises the temperature of the reaction mixture to 30°–35° C. After an additional stirring for 4 hours a precipitate is obtained that is isolated by filtration and is washed with 50 ml of water. The solid is crystallized once from ether, melting point (free base): 110°–113° C. This substance is dissolved in absolute ethanol. To the solution are added 40.5 ml of a 7.7 N HCl solution in absolute ethanol, followed by the addition of 600 ml of ether. The precipitate formed is filtered and recrystallized from ethanol-ether. Yield: 57 g; melting point HCl salt 170°–172° C. Substitution of maleic acid for HCl yields the corresponding maleate, melting point 106°–107° C.

b. By using a solution of N-methylhydroxylamine in alcohol instead of hydroxylamine.HCl, the compound N-hydroxy-N-methyl-benzocyclobutene-1-carboxamidine.HCl is obtained; melting point 184°–185° C.

In the same manner as described above the HCl salt, fumarate and maleate of O-methyl-benzocyclobutene-1-carboxamidoxime is obtained if instead of hydroxylamine HCl an alcoholic solution of hydroxylaminemethylether is applied.

In the same manner as described above the compound O-benzyl-benzocyclobutene-1-carboxamidoxime.HCl is obtained if instead of hydroxylamine.HCl an alcoholic solution of hydroxylaminebenzylether is applied.

EXAMPLE II

Resolution of racemic (±)-benzocyclobutene-1-carboxamidoxime

To a solution of 20 g of the free base obtained in Example I in 50 ml of methanol, 9.6 g of L(−)mandalic acid are added and dissolved by heating.

The salt that precipitates by cooling is isolated and recrystallised from ethanol-isopropanol (2:1).

Hydrolysis of the salt obtained in this way with NaOH yields 3 g of (+)-benzocyclobutene-1-carboxamidoxime $[\alpha]_D^{20} = +42°$ ($c=1$ in chloroform).

The addition of an equivalent quantity of HCl in absolute alcohol yields the hydrochloric salt (2.4 g) with a melting point of 159°–161° C and $[\alpha]_D^{20} = +77°$ ($c=1.05$ in methanol).

The filtrate of the mother-liquor is treated with sodium-bicarbonate. The free base obtained is treated with D(+) mandalic acid in alcohol in the same manner as described hereinbefore.

The purified salt is likewise treated with NaOH yielding 2.5 g of (−)-benzocyclobutene-1-carboxamidoxime: $[\alpha]_D^{20} = -42°$ ($c=1$ in chloroform).

The HCl salt obtained from it (2.5 g) has a melting point of 159°–161° C and $[\alpha]_D^{20} = -77°$ ($c=0.98$ in methanol).

EXAMPLE III

Benzocyclobutene-1-carboxamidoxime-O-carbamate 3.0 g of benzocyclobutene-1-carboxamidoxime.HCl, obtained in Example I, are dissolved in 10 ml water whereupon the solution is cooled down to 5° C. To this solution a solution of 3 g potassiumcyanate in 10 ml water is added on. After a 30 min.'s period of stirring the precipitate formed is filtered off and dried. The white powder is recrystallised from benzene/cyclohexane.

Yield: 1.3 g; melting point 106°–107° C;
Rf in toluene:acetone (6:4) = 0.45 on $SiO_2$.

EXAMPLE IV

Benzocyclobutene-1-carboxamidoxime-O-(N-methylcarbamate)

To a suspension of 8.1 g benzocyclobutene-1-carboxamidoxime, (obtained in Example I) in 50 ml benzene a solution of 2.75 g methylisocyanate in 25 ml benzene is added on at about 8° C. (The temperature should be kept below 10° C). The mixture is stirred for an additional hour and then distilled off under diminished pressure. The residue is recrystallised from ethylacetate.

Yield: 4.0 g; melting point 134°–135° C.
Rf in chloroform:methanol (95:5) = 0.44 on $SiO_2$.

In the same manner is prepared the substance:
4,5-methylenedioxy-benzocyclobutene-1-carboxamidoxime-O-(N-methylcarbamate); melting point 170°–171° C
and 4,6-dimethyl-benzocyclobutene-1-carboxamidoxime-O-(N-methylcarbamate); melting point 103°–105° C.

EXAMPLE V a. Indane-1-carboxamidoxime hydrochloride 6.4 g of 1-cyanoindane (J. Org. Chem. 27 3836 (1962)) are refluxed with 83 ml of 0.8 N hydroxylamine in absolute ethanol for 2.5 hours. The solvent is then evaporated and the residue dissolved in ethanol, after which the solvent is evaporated again. An equivalent quantity of 6.5 N HCl in absolute ethanol is firstly added on to the residue, followed by the addition of ether. The precipitate formed is filtered off and crystallized from ethanol/ether.

Yield: 3 g; melting point 188°–190° C.
Rf in methanol:acetic acid (98:2) = 0.80 on $SiO_2$.

In a similar manner are prepared:
N-hydroxy-N-methyl-indane-1-carboxamidine.HCl
N-hydroxy-N-phenyl-indane-1-carboxamidine.HCl and
N-hydroxy-N-p-tolyl-indane-1-carboxamidine.HCl.

EXAMPLE VI a. 1,2,3,4,-tetrahydronaphthalene-1-carboxamidoxime hydrochloride

A mixture of 6.9 g of 1-cyano-1,2,3,4-tetrahydronaphthalene (J. Org. Chem. 27, 3836 (1962)) and 165 ml of 0.4 N hydroxylamine in absolute ethanol is refluxed for 7 hours. After evaporation of the solvent in vacuo the excess of hydroxylamine is removed by repeated evaporation with ethanol. The residue is treated with 6.4 ml 6.8 N HCl in ethanol. The precipitate formed is recrystallised from ethanol-ether.

Yield: 4.3 g; melting point 195°–197° C.
Rf in toluene:ethanol (7:3) = 0.68 on $SiO_2$.

b. In a similar manner are prepared:
N-hydroxy-N-methyl-1,2,3,4-tetrahydronaphthalene-1-carboxamidine.HCl,
N-hydroxy-N-p-tolyl-1,2,3,4-tetrahydronaphtalene-1-carboxamidine.HCl.

EXAMPLE VII 1-methyl-benzocyclobutene-1-carboxamidoxime hydrochloride 2.9 g of 1-methyl-1-cyano-benzocyclobutene (J. Org. Chem. 37, 820 (1972)) are mixed with 94 ml of 0.3 n hydroxylamine in absolute ethanol and stirred at room temperature for 16 hours. The reaction mixture is evaporated, which procedure — after adding alcohol to the residue — is repeated some times to remove the excess of hydroxylamine.

The residue is then stirred for some minutes in cyclohexane, after which the solid substance is filtered off and dissolved in alcohol. 2.5 ml 6.5 N HCl in ethanol are added on to this solution followed by the addition of ether yielding a precipitate that is recrystallised from absolute ethanol/ether.

Yield: 2.2 g; melting point 154°–156° C. Rf in methanol:acetic acid (98:2) = 0.80 on $SiO_2$.

In the same manner are prepared the free bases:
1-benzyl-benzocyclobutene-1-carboxamidoxime; melting point 129°–130° C,
1-isopropyl-benzocyclobutene-1-carboxamidoxime; melting point 109°–110° C.

EXAMPLE VIII

N-methyl-benzocyclobutene-1-carboxamidoxime hydrochloride a. A solution of 33.3 g benzocyclobutene-1-carbonylchloride (J. Med. Chem. 8, 255 (1965)) in ether is added dropwise to a solution of 100 ml 4 N methylamine in absolute ethanol. After stirring for 15 minutes the mixture is poured into water and extracted with methylene chloride. The residue obtained after drying and evaporating the extracts is recrystallised from toluene.

Yield: 25.3 g of N-methyl-benzocyclobutene-1-carboxamide. Melting point 106°–109° C.

b. 31.8 g of the compound obtained in (a) are dissolved in 800 ml of dioxane and after the addition of 12.4 g of solid sodium sulphide stirred for 10 minutes. 44.4 g of $P_2S_5$ are then added, whereupon the mixture is heated and stirred for 2 hours at 80° C.

After cooling the mixture it is poured into water after which the resulting mixture is extracted with $CH_2Cl_2$.

The residue obtained by washing, drying and evaporating the extracts is recrystallised from ethanol-water (1:1).

Yield: 32 g of N-methyl-benzocyclobutene-1-carbothionamide. Melting point 65°–68° C.

c. The product (32 g) obtained in (b) is dissolved in benzene whereafter 28.4 g of methyliodide are added while stirring. The mixture is refluxed for 30 minutes and then cooled down to 0° C.

The precipitate formed is filtered off.

Yield: 46.8 g of N,S-dimethyl-benzocyclobutene-1-carboisothionamide.hydroiodide.

d. 3.2 g of the product obtained in (c) are dissolved in 15 ml of 0.8 N hydroxylamine in absolute ethanol and stirred for 4 hours at room temperature.

The hydroiodide obtained by evaporating the mixture is treated with 4 N NaOH, whereafter the mixture is extracted with methylenechloride.

After drying and evaporation of the extracts an equivalent quantity of 6.5 N HCl in absolute ethanol is added on to the residue. By adding ether a precipitate is obtained that is filtered off and recrystallised from ethanol-ether.

Yield: 0.5 g of N-methyl-benzocyclobutene-1-carboxamidoxime hydrochloride; melting point 148°–150° C.

Rf in methanol:acetic acid (98:2) = 0.75 on $SiO_2$.

EXAMPLE IX a. In the same manner as described in Example VIII (a) are prepared:

N-methyl-indane-1-carboxamide, indane-1-carboxamide, N-benzyl-indane-1-carboxamide and N-ethyl-benzocyclobutene-1-carboxamide, whereafter these compounds are converted in the manner as mentioned in VIII (b) and (c) into resp.:

N,S-dimethyl-indane-1-carboisothionamide.HJ; S-methyl-indane-1-carboisothionamide.HJ; N-benzyl, S-methyl-indane-1-carboisothionamide.HJ and N-ethyl, S-methyl-benzocyclobutene-1-carboisothionamide.HJ.

b. The isothionamides obtained in (a) are converted with hydroxylamine in the manner as described in Example VIII (d) into resp.: N-methyl-indane-1-carboxamidoxime, indane-1-carboxamidoxime, N-benzyl-indane-1-carboxamidoxime and N-ethyl-benzocyclobutene-1-carboxamidoxime.

c. By having the compounds obtained in (a) reacted in the manner as mentioned in Example VIII (d) with an alcoholic solution of N-methylhydroxylamine the following compounds are obtained:

N,N'-dimethyl, N-hydroxy-indane-1-carboxyamidine, N-hydroxy, N-methyl-indane-1-carboxamidine, N-benzyl, N'-hydroxy-N'-methyl-indane-1-carboxamidine, and N-ethyl, N'-hydroxy, N'-methyl-benzocyclobutene-1-carboxamidine.

EXAMPLE X

Benzocyclobutene-1-methylcarboxamidoxime.hydrochloride a. 1-cyanomethyl-benzocyclobutene A solution of 13 g of 1-hydroxymethyl-benzocyclobutenetosylate (J. Med. Chem. 8, 256 (1965)) in 5 ml of dimethylsulfoxide is added to a solution of 2.6 g of sodium cyanide in 26 ml of dimethylsulfoxide. This mixture is heated at 65° C for 1 hour.

Then the reaction mixture is poured into 300 ml of water and extracted with ether.

The oily residue, obtained after drying and evaporation of the ether extracts, is distilled in vacuo. The product (5.3 g of oil) has a boiling-point of 104°–105° C at 2 mm Hg.

Rf in toluene:ethanol (8:2) = 0.9 on $SiO_2$.

b. Benzocyclobutene-1-methylcarboxamidoxime.hydrochloride 3.25 g of the oil obtained in (a) are added to 50 ml of a 4 N hydroxylamine solution in absolute methanol.

After refluxing for 3 hours the reaction mixture is evaporated and after adding absolute ethanol to the residue evaporated again.

The residue is then dissolved in ether and the solution obtained is washed with water, dried on $MgSO_4$ and evaporated. To the residue are added 10 ml of absolute ethanol and an equivalent quantity 8 N HCl in absolute ethanol.

Addition of ether to this solution facilitates the precipitation of the title compounds. The precipitate formed is filtered off.

Melting point 161°–163° C.

Rf in toluene (8:2) = 0.40 on $SiO_2$.

EXAMPLE XI in a similar manner as indicated in Example X (b) the following compounds are prepared:

5-methoxy-benzocyclobutene-1-carboxamidoxime hydrochloride, 6-methoxy-indane-1-carboxamidoxime.hydrochloride, 4,5-dimethoxy-benzocyclobutene-1-carboxamidoxime.hydrochloride, 6,7-dimethoxy-1,2,3,4-tetrahydronaphtalene-1-carboxamidoxime.HCl, 5-nitro-benzocyclobutene-1-carboxamidoxime.HCl, 5-chloro-benzocyclobutene-1-carboxamidoxime.HCl, 5-amino-benzocyclobutene-1-carboxamidoxime.HCl, 5-hydroxy-benzocyclobutene-1-carboxamidoxime.HCl, 4,5-dihydroxy-benzocyclobutene-1-carboxamidoxime.HCl, 4,5-methylenedioxy-benzocyclobutene-1-carboxamidoxime.HCl, 4-chloro-6-methyl-benzocyclobutene-1-carboxamidoxime.HCl, 3,4,5,6-tetramethyl-benzocyclobutene-1-carboxamidoxime.HCl, N-hydroxy-N-methyl-5-methoxy-benzocyclobutene-1-carboxamidine.HCl.

EXAMPLE XII 4,6-dimethyl-benzocyclobutene-1-carboxamidoxime.HCl a. 1-cyano-4,6-dimethyl-benzocyclobutene 12 g of sodium cyanide are added to 20.5 g of crude 1-chloro-4,6-dimethyl-benzocyclobutene (Org. Preparations & Procedures 2, 89 (1970)) dissolved in 75 ml of dimethylsulfoxide.

The reaction mixture is heated at 70° C for one night. After cooling the mixture it is poured into water and extracted with hexane. The hexane-extract is washed to neutral, dried and evaporated.

After distillation and crystallisation the residue from petroleum-ether, 4 g of 1-cyano-4,6-dimethyl-benzocyclobutene are obtained. Melting point 62°–64° C.

b. 4,6-dimethyl-benzocyclobutene-1-carboxamidoxime.HCl 9 ml of a 4 N solution of hydroxylamine in absolute methanol are added to 2.85 g of the compound obtained in (a). After refluxing for 2 hours the excess of hydroxylamine is removed by evaporating.

The residue is extracted with ether and the ether-extracts washed with water. The residue obtained after evaporation is converted with 3.5 ml of 5.5 N HCl in absolute alcohol into the hydrochloride salt.

Yield: 2.4 g; melting point 174°–176° C.

Rf in toluene:ethanol (8:2) = 0.49 on $SiO_2$.

EXAMPLE XIII 3,3-dimethylindane-1-carboxamidoxime.hydrochloride a. Dry HCl gas is passed for 4.5 hours through a solution of 27 g of 3,3-dimethyl-indanol-1, Can. J. Chem. 42, 1718 (1964), in hexane, to which 22.5 g of $CaCl_2$ are added. The reaction mixture is filtered and the filter washed with hexane. The filtrate is evaporated at a low temperature. 29.6 g of the crude chloro compound is obtained. Rf in toluene:ethylacetate (7:3) = 0.85 on $SiO_2$.

b. 12.5 g of sodium cyanide are added to 1-chloro-3,3-dimethyl-indane obtained in (a), that is dissolved in 125 ml of dimethylsulfoxide. The mixture is heated at 60° C for 1 hour and then at 70° C for 2 hours. After cooling and pouring the mixture into water, the aqueous mixture is extrated with hexane and the hexane-extracts washed, dried and evaporated (oil). After distillation of the oil in vacuo, 22.3 g of 1-cyano-3,3-dimethylindane are obtained with a boiling point of 95°–97°/0.1 mm Hg. Rf in toluene:ethylacetate (9:1) = 0.68 on $SiO_2$.

c. 190 ml of 0.4 N hydroxylamine in ethanol are added to 8.6 g of the compound obtained in (b).

The mixture is refluxed for 7 hours and then evaporated. The residue is dissolved in ethanol and the solution is evaporated again. This procedure is repeated several times in order to remove the excess of hydroxylamine completely. The residue obtained is then treated with 7.75 ml of 6.8 n HCl in ethanol. The precipitate is recrystallized from ethanol-ether.

Yield: 7.6 g; melting point 197°–199° C.

Rf in toluene:ethylacetate (7:3) = 0.70 on $SiO_2$.

EXAMPLE XIV

Benzocyclobutene-1-carboxamidoxime-O-(N,N-dimethylcarbamate)

2.4 g of benzocyclobutene-1-carboxamidoxime is dissolved in 30 ml chloroform. To this solution is added 1.6 g of triethylamine and 1.6 g of dimethylcarbamoylchloride. The resulting mixture is refluxed for about an hour and then evaporated. The residue is diluted with water and after that extracted with benzene. The benzene-extracts are dried and evaporated. The residue obtained is crystallized from benzene/cyclohexane.

Yield: 1.3 g; melting point 145°–147° C.

Rf in methylenechloride:aceton (7:3) = 0.64 on $SiO_2$.

In the same manner is prepared:
4,5-methylenedioxy-benzocyclobutene-1-carboxamidoxime-O-(N,N-dimethylcarbamate).

EXAMPLE XV 4,5-methylenedioxy-benzocyclobutene-1-carboxamidoxime-O-acetate

To a solution of 0.5 g of 4,5-methylenedioxy-benzocyclobutene-1-carboxamidoxime in 4 ml of pyridine is added 0.26 g of acetylchloride. After stirring at ambient temperature for 3 hours the reaction mixture is poured into ice-water and then extracted with ether. The ether extracts are washed with water, dried and evaporated. The residue is crystallized from ether.

Yield: 0.4 g; m.p. 152°–154° C.

Rf in methylenechloride-methanol (97,5:2,5) on silica = 0.33.

In the same manner are prepared:
4,5-methylenedioxy-benzocyclobutene-1-carboxamidixime-O-(2-phenylacetate)
4,5-methylenedioxy-benzocyclobutene-1-carboxamidoxime-O-propionate
5,6-methylenedioxy-indane-1-carboxamidoxime-O-acetate.

EXAMPLE XVI 4,5-methylenedioxy-benzocyclobutene-1-carboxamidoxime. HCl 104 g Of 1-cyano-4,5-methylenedioxy-benzocyclobutene are added to 500 ml of a 4N hydroxylamine solution in absolute methanol. This solution is prepared from 500 ml of methanol, 14 g of lithium and 140 g of $NH_2OH.HCl$. The precipitated LiCl is removed by suction.

The reaction mixture is refluxed for 3 hours and then evaporated. After addition of ethanol to the residue the solution is again evaporated till dry.

The residue is dissolved in ether and the solution obtained is washed with water, dried on $MgSO_4$ and evaporated (yield 110.5 g). To a small part of the residue are added 10 ml of absolute ethanol and an equivalent quantity of HCl in absolute ethanol. Addition of ether to this solution facilitates the precipitation of the compound. The precipitate formed is filtered off, m.p. 190° C dec.

Rf in toluene-ethanol on silica = 0.58.

In the same manner are prepared:
4,5-ethylenedioxy-benzocyclobutene-1-carboxamidoxime.HCl. 5,6-methylenedioxy-indane-1-carboxamidoxime.HCl.

I claim:

1. A compound of the formula:

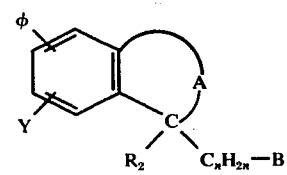

in which

B is N-hydroxy-amidino of the group consisting of

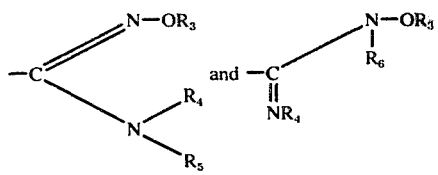

A is selected from the group consisting of methylene, lower alkyl-substituted methylene, ethylene, lower alkyl substituted ethylene, propylene and lower alkyl substituted propylene, said lower alkyl containing from 1 to 6 carbon atoms;

Q and Y together form an alkylenedioxy group, in which the alkylene group has 1 to 4 carbon atoms;

$C_nH_{2n}$ is alkylene containing 1 to 4 carbon atoms or a single bond, $R_2$ is selected from the group consisting of hydrogen, alkyl containing 1 to 6 carbon atoms, aryl and phenylalkyl the alkyl group of which contains 1 to 4 carbon atoms;

$R_3$ is selected from the group consisting of hydrogen, alkyl containing 1 to 6 carbon atoms, phenylalkyl the alkyl group of which contains 1 to 4 carbon atoms, and acyl derived from an organic carboxylic acid containing 1 to 18 carbon atoms;

$R_4$ and $R_5$ are selected from the group consisting of hydrogen, alkyl containing 1 to 6 carbon atoms and phenylalkyl the alkyl group of which contains 1 to 4 carbon atoms;

$R_6$ is selected from the group consisting of hydrogen, alkyl containing 1 to 6 carbon atoms, phenyl, methylphenyl, benzyl and methylbenzyl;

and the pharmaceutically acceptable acid addition salts thereof.

2. A compound according to claim 1 of the formula:

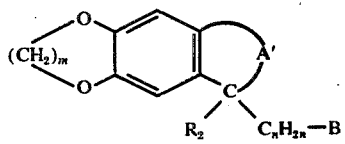

in which
A' is selected from the group consisting of methylene, lower alkyl substituted methylene, ethylene and lower alkyl substituted ethylene, said lower alkyl group containing from 1 to 6 carbon atoms;
m is selected from the values 1, 2, 3 and 4, and
$R_2$, $C_nH_{2n}$ and B have the meanings indicated in claim 1
and the pharmaceutically acceptable acid addition salts thereof.

3. A compound according to claim 1 of the formula:

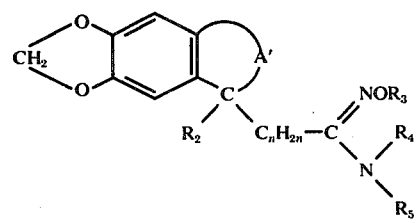

in which
$R_3$ represents an acyl group derived from an organic carboxylic acid containing 1 to 18 carbon atoms;
A' has the meaning indicated in claim 2, and
$R_2$, $C_nH_{2n}$, $R_4$ and $R_5$ have the meanings indicated in claim 1,
and the pharmaceutically acceptable acid addition salts thereof.

4. A compound of the formula:

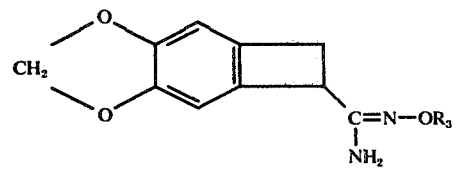

in which
$R_3$ is selected from carbamoyl, N-methylcarbamoyl and N,N-dimethylcarbamoyl
and the pharmaceutically acceptable acid addition salts thereof.

* * * * *